United States Patent
Dodda et al.

(10) Patent No.: US 9,376,427 B2
(45) Date of Patent: Jun. 28, 2016

(54) PROCESS FOR PREPARING RIVAROXABAN USING INTERMEDIATES

(75) Inventors: Mohan Rao Dodda, Hyderabad (IN); Venkat Reddy Buthukuri, Hyderabad (IN)

(73) Assignee: Symed Labs Limited (IN)

( * ) Notice: Subject to any disclaimer, the term of this patent is extended or adjusted under 35 U.S.C. 154(b) by 50 days.

(21) Appl. No.: 14/397,551

(22) PCT Filed: May 2, 2012

(86) PCT No.: PCT/IN2012/000321
§ 371 (c)(1),
(2), (4) Date: Oct. 28, 2014

(87) PCT Pub. No.: WO2013/164833
PCT Pub. Date: Nov. 7, 2013

(65) Prior Publication Data
US 2015/0126733 A1    May 7, 2015

(51) Int. Cl.
*C07D 413/14*    (2006.01)
*C07D 333/38*    (2006.01)
*C07D 333/40*    (2006.01)

(52) U.S. Cl.
CPC ............ *C07D 413/14* (2013.01); *C07D 333/38* (2013.01)

(58) Field of Classification Search
None
See application file for complete search history.

(56) References Cited

U.S. PATENT DOCUMENTS

| 2007/0149522 | A1 | 6/2007 | Thomas |
| 2010/0298293 | A1 | 11/2010 | Allerheiligen et al. |
| 2011/0034465 | A1* | 2/2011 | Bodhuri ............ A61K 31/5377 514/236.8 |
| 2011/0288294 | A1 | 11/2011 | Nonnenmacher et al. |

OTHER PUBLICATIONS

International Search Report for PCT/IN2012/000321 mailed Nov. 19, 2012.
International Search Report and Written Opinion dated Nov. 19, 2012 of PCT/IN2012/000321.

* cited by examiner

*Primary Examiner* — Laura L. Stockton
(74) *Attorney, Agent, or Firm* — Caesar Rivise, PC

(57) ABSTRACT

The present inventors have surprisingly found that rivaroxaban of formula I can be prepared in a one-pot process, in high purity and with high yield, by reacting 5-chlorothiophene-2-carboxylic acid or a salt thereof with a sulfonylating agent to produce a sulfonyl ester intermediate, which is then condensed with 4-[4-[(SS)-5-(aminomethyl)-2-oxo-1,3-oxazolidin-3-yl]phenyl]morpholine-3-one or an acid addition salt thereof to produce rivaroxaban.

18 Claims, No Drawings

PROCESS FOR PREPARING RIVAROXABAN USING INTERMEDIATES

FIELD OF THE INVENTION

The present invention relates to a novel, commercially viable and industrially advantageous process for the preparation of rivaroxaban, in high yield and purity, using novel intermediates.

BACKGROUND OF THE INVENTION

PCT Publication No. WO01/47919A1 (corresponding US equivalent U.S. Pat. No. 7,585,860) discloses a variety of substituted oxazolidinone derivatives and their salts, processes for their preparation, pharmaceutical compositions comprising the derivatives, and methods of use thereof. These compounds are anticoagulants which inhibit the blood coagulation factor Xa with increased selectivity. Among them, Rivaroxaban, 5-chloro-N-[[(5S)-2-oxo-3-[4-(3-oxomorpholin-4-yl)phenyl]oxazolidin-5-yl]methyl]thiophene-2-carboxamide, acts as inhibitor of clotting factor Xa and which is used as agent for the prophylaxis and/or treatment of thromboembolic disorders, in particular myocardial infarction, angina pectoris, reocclusions and restenoses after angioplasty or aortocoronary bypass, stroke, transient ischaemic attacks, peripheral arterial occlusive diseases, pulmonary embolisms or deep venous thromboses. Rivaroxaban is represented by the following structural formula I:

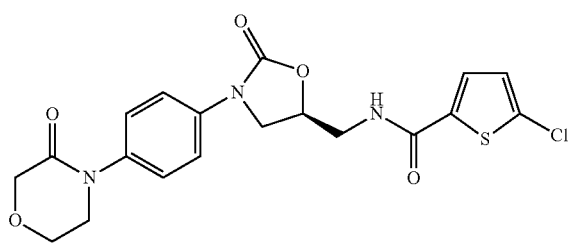

Rivaroxaban is sold by Bayer under the brand name Xarelto® and it is orally administered as tablets containing 10 mg of rivaroxaban.

Various processes for the preparation of rivaroxaban, its intermediates, and related compounds are disclosed in U.S. Pat. Nos. 7,585,860; 7,351,823 and 7,816,355; PCT Publication Nos. WO2011/012321, WO2011/080341 and WO2011/098501; and J. Med. Chem. 2005, 48, 5900-5908.

According to U.S. Pat. No. 7,585,860 (hereinafter referred to as the '860 patent), rivaroxaban is prepared by reacting 4-[4-[(5S)-5-(aminomethyl)-2-oxo-1,3-oxazolidin-3-yl] phenyl]morpholine-3-one with 5-chlorothiophene-2-carbonyl chloride in the presences of excess amounts of pyridine. As per the process exemplified in example 44 of the '860 patent, rivaroxaban is prepared by drop-wise addition of 5-chlorothiophene-2-carbonyl chloride to a solution of 4-[4-[(5S)-5-(aminomethyl)-2-oxo-1,3-oxazolidin-3-yl]phenyl] morpholine-3-one in pyridine at 0° C. under argon, followed by removal of ice-cooling and stirring the reaction mixture at room temperature for 1 hour and then admixing with water. After addition of dichloromethane and phase separation, the aqueous phase was extracted with dichloromethane. The combined organic phases were dried, filtered, and evaporated in vacuo. The residue was purified by Flash chromatography (dichloromethane/methanol mixtures) to produce rivaroxaban.

According to U.S. Pat. No. 7,351,823 (hereinafter referred to as the '823 patent), rivaroxaban is prepared by reacting 4-[4-[(5S)-5-(aminomethyl)-2-oxo-1,3-oxazolidin-3-yl] phenyl]morpholine-3-one hydrochloride salt with 5-chlorothiophene-2-carbonyl chloride in the presence of an inorganic base, preferably sodium carbonate, in a solvent selected from the group consisting of ether, alcohol, ketone and water or in a mixture thereof. As per the process exemplified in the '823 patent, the preparation of rivaroxaban is carried out in three steps. According to the first step, 5-chlorothiophene-2-carbonyl chloride is prepared by reacting 5-chlorothiophene-2-carboxylic acid with thionyl chloride in toluene at a temperature of 75 to 80° C. According to the second step, 4-[4-[(5S)-5-(aminomethyl)-2-oxo-1,3-oxazolidin-3-yl]phenyl] morpholine-3-one hydrochloride salt is reacted with 5-chlorothiophene-2-carbonyl chloride (30% strength solution in toluene) in the presence of sodium carbonate in a solvent mixture containing water and acetone to produce crude rivaroxaban. In third step, the solvent-containing crude product is purified by recrystallization from acetic acid.

The processes for the preparation of rivaroxaban described in the aforementioned prior art suffer from disadvantages such as the use of highly hazardous materials like thionyl chloride and pyridine, and use of tedious and cumbersome procedures like low temperatures, multiple process steps, column chromatographic purifications, multiple isolations/re-crystallizations, recrystallization using corrosive acids like acetic acid, and thus resulting in a poor product yield and quality. Methods involving column chromatographic purifications are generally undesirable for large-scale operations, thereby making the process commercially unfeasible.

The main drawback of the processes for the preparation of rivaroxaban described in the aforementioned prior art is that the processes involve the use of highly corrosive and unstable acid chloride intermediate, 5-chlorothiophene-2-carbonyl chloride. Use of this unstable acid chloride intermediate is not advisable for scale up operations due to handling difficulties. Moreover, the process for the preparation of the acid chloride intermediate requires the use of highly hazardous and toxic reagents like thionyl chloride, phosgene and oxalyl chloride, which are highly corrosive and dangerous to environment. Handling of these reagents is very difficult on commercial scale operations.

The process for the preparation of rivaroxaban described in the '860 patent involves the use of excess amounts of pyridine, which is highly toxic chemical and dangerous to human health.

Based on the aforementioned drawbacks, the prior art processes have been found to be unsuitable for the preparation of rivaroxaban at lab scale and in commercial scale operations.

A need remains for an improved, commercially viable and environmentally friendly process of preparing rivaroxaban with high yield and purity, to resolve the problems associated with the processes described in the prior art, and that will be suitable for large-scale preparation. Desirable process properties include non-hazardous conditions, environmentally friendly and easy to handle reagents, reduced process steps, reduced reaction time periods, reduced cost, greater simplicity, increased purity, and increased yield of the product, thereby enabling the production of rivaroxaban in high purity and with high yield.

SUMMARY OF THE INVENTION

The present inventors have surprisingly found that rivaroxaban of formula I can be prepared in a one-pot process, in high purity and with high yield, by reacting 5-chlorothiophene-2-carboxylic acid or a salt thereof with a sulfonylating agent to produce a sulfonyl ester intermediate, which is then condensed with 4-[4-[(5S)-5-(aminomethyl)-2-oxo-1, 3-oxazolidin-3-yl]phenyl]morpholine-3-one or an acid addition salt thereof to produce rivaroxaban.

In one aspect, provided herein is an efficient, industrially advantageous and environmentally friendly process for the preparation of rivaroxaban, in high yield and with high chemical and enantiomeric purity, using novel intermediates. The process disclosed herein avoids the tedious and cumbersome procedures of the prior processes, thereby resolving the problems associated with the processes described in the prior art, which is more convenient to operate at lab scale and in commercial scale operations.

In another aspect, provided herein are novel sulfonyl ester compounds of formula III:

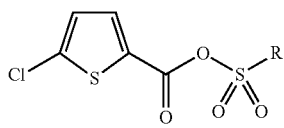

III wherein 'R' is an alkyl, cycloalkyl, haloalkyl, aralkyl, or substituted or unsubstituted aryl group.

In another aspect, the present invention also encompasses the use of novel sulfonyl ester intermediates of formula III disclosed herein for preparing rivaroxaban or a stereochemically isomeric form or a racemic mixture thereof.

The process for the preparation of rivaroxaban disclosed herein has the following advantages over the processes described in the prior art:
i) the process is carried out in a single pot using novel intermediates, and it involves shorter reaction times and reduced quantities of reagents and solvents;
ii) the process avoids the use of hazardous and corrosive chemicals like pyridine, thionyl chloride, and unstable acid chloride intermediate;
iii) the process avoids the use of tedious and cumbersome procedures like column chromatographic purifications, multiple isolations/recrystallizations, and recrystallizations using corrosive acids such as acetic acid;
iv) the process involves easy work-up methods and simple isolation processes, and there is a reduction in chemical waste;
v) the purity of the product is increased without additional purifications; and
vi) the overall yield of the product is increased.

DETAILED DESCRIPTION OF THE INVENTION

According to one aspect, there is provided a one-pot process for preparing rivaroxaban, 5-chloro-N-[[(5S)-2-oxo-3-[4-(3-oxomorpholin-4-yl)phenyl]oxazolidin-5-yl]methyl]thiophene-2-carboxamide, of formula I:

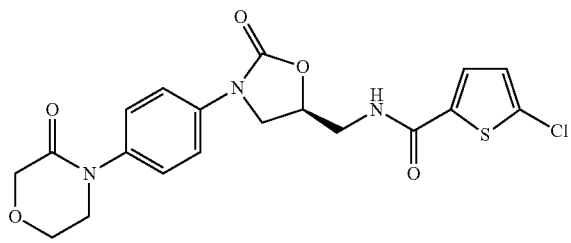

I or a stereochemically isomeric form or a racemic mixture thereof, comprising:
a) reacting 5-chlorothiophene-2-carboxylic acid of formula IV:

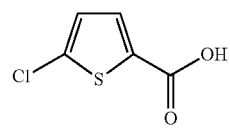

IV or a salt thereof,
with a sulfonylating agent of formula Va or Vb:

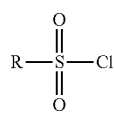

Va

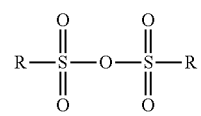

Vb wherein 'R' is an alkyl, cycloalkyl, haloalkyl, aralkyl, or substituted or unsubstituted aryl group; to produce a sulfonyl ester compound of formula III:

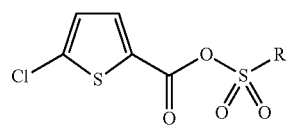

III wherein R is as defined above; and
b) reacting the sulfonyl ester compound of formula III with 4-[4-[(5S)-5-(aminomethyl)-2-oxo-1,3-oxazolidin-3-yl]phenyl]morpholine-3-one of formula II:

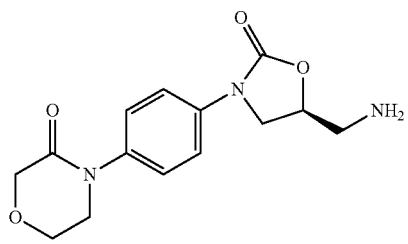

II or a stereochemically isomeric form or a racemic mixture thereof, or an acid addition salt thereof, to produce the rivaroxaban of formula I or a stereochemically isomeric form or a racemic mixture thereof.

The structural formula of rivaroxaban contains one chiral centre and thus exists as two optical isomers, i.e. enantiomers (R & S-isomers). The process disclosed herein encompasses the preparation of both enantiomers and mixtures thereof in all proportions.

The term "alkyl", as used herein, denotes an aliphatic hydrocarbon group which may be straight or branched having 1 to 12 carbon atoms in the chain. Preferred alkyl groups have 1 to 6 carbon atoms in the chain. The alkyl may be substituted with one or more "cycloalkyl groups". Exemplary alkyl groups include methyl, ethyl, n-propyl, isopropyl, n-butyl, iso-butyl, t-butyl, and n-pentyl.

The term "cycloalkyl", as used herein, denotes a non-aromatic mono- or multicyclic ring system of 3 to 10 carbon atoms, preferably of about 5 to about 10 carbon atoms. Exemplary monocyclic cycloalkyl groups include cyclopentyl, cyclohexyl, cycloheptyl and the like.

The term "aralkyl", as used herein, denotes an aryl-alkyl group wherein the aryl and alkyl are as herein described. Preferred aralkyls contain a lower alkyl moiety. Exemplary aralkyl groups include benzyl, 2-phenethyl and naphthalen-emethyl.

The term "aryl", as used herein, denotes an aromatic monocyclic or multicyclic ring system of 6 to 10 carbon atoms. The aryl is optionally substituted with one or more "ring system substituents" which may be the same or different, and are as defined herein. Exemplary aryl groups include phenyl, tolyl or naphthyl.

Specifically, the group 'R' in the compounds of formulae III, Va and Vb is selected from the group consisting of methyl, ethyl, propyl, isopropyl, isobutyl, chloromethyl, fluoromethyl, trifluoromethyl, phenyl, p-tolyl, benzyl, 4-nitrophenyl, 4-chlorophenyl, 3-nitrophenyl, 4-chlorobenzyl, and the like; and most specifically, R is methyl or p-tolyl.

The sulfonyl ester compounds of formula III are novel and form another aspect of the present invention.

The use of the sulfonyl ester compounds of formula III in the process for manufacture of rivaroxaban, or a stereochemically isomeric form or a racemic mixture thereof, is novel and forms further aspect of the present invention.

In one embodiment, the one-pot process disclosed herein is carried out in the presence of a solvent or a mixture of solvents.

Exemplary solvents used in the one-pot process include, but are not limited to, a chlorinated hydrocarbon, an ester, a cyclic ether, an aliphatic ether, a hydrocarbon, a polar aprotic solvent, a nitrile, an alcohol, and mixtures thereof; and most specifically a chlorinated hydrocarbon solvent.

Specifically, the solvent is selected from the group consisting of dichloromethane, dichloroethane, chloroform, carbon tetrachloride, ethyl acetate, methyl acetate, isopropyl acetate, tert-butyl methyl acetate, ethyl formate, tetrahydrofuran, 2-methyl tetrahydrofuran, dioxane, diethyl ether, diisopropyl ether, methyl tert-butyl ether, monoglyme, diglyme, n-pentane, n-hexane, n-heptane, cyclohexane, toluene, xylene, acetonitrile, propionitrile, 4-methylmorpholine, N,N-dimethylformamide, N,N-dimethylacetamide, dimethylsulfoxide, methanol, ethanol, isopropanol, n-butanol, and mixtures thereof. A most specific solvent is dichloromethane.

In one embodiment, the one-pot process disclosed herein is carried out in the presence of a base. Specifically, the base is an organic or inorganic base, and most specifically an organic base.

Exemplary organic bases include, but are not limited to, trimethylamine, tributylamine, triethylamine, diisopropylethylamine, N-methylmorpholine, 4-(N,N-dimethylamino) pyridine and 1-alkylimidazole. Specific organic bases are 1-alkylimidazole and 4-(N,N-dimethylamino)pyridine, and more specifically 1-methylimidazole.

Exemplary inorganic bases include, but are not limited to, hydroxides, alkoxides, bicarbonates and carbonates of alkali or alkaline earth metals. Specific inorganic bases are sodium hydroxide, calcium hydroxide, magnesium hydroxide, potassium hydroxide, lithium hydroxide, sodium carbonate, potassium carbonate, sodium bicarbonate, potassium bicarbonate, lithium carbonate, sodium tert-butoxide, sodium isopropoxide and potassium tert-butoxide.

In one embodiment, the base is used, in the process disclosed herein, in a ratio of about 1 to 4 equivalents, specifically about 1.5 to 3.5 equivalents, with respect to the compound of formula IV in order to ensure a proper course of the reaction.

In another embodiment, the 5-chlorothiophene-2-carboxylic acid of formula IV is used in the form a salt. The salt of the compound of formula IV is derived from an organic or inorganic base selected from the group as described above. Specifically, the salt of the compound of formula IV is derived from an organic base.

Exemplary acid addition salts of the amine compound of formula II include, but are not limited to, hydrochloride, hydrobromide, sulfate, nitrate, phosphate, acetate, propionate, oxalate, succinate, maleate, fumarate, benzenesulfonate, toluenesulfonate, citrate, and tartrate.

The overall one-pot process is carried out at a temperature of about −15° C. to about the boiling temperature of the solvent used, specifically at a temperature of about −10° C. to about 50° C., and more specifically at a temperature of about −5° C. to about 30° C. The reaction time may vary from about 30 minutes to about 15 hours, specifically from about 1 hour to about 10 hours, and more specifically from about 2 hours to about 5 hours.

The reaction mass containing the rivaroxaban of formula I obtained may be subjected to usual work up such as a washing, an extraction, an evaporation, a pH adjustment etc., followed by isolation and/or recrystallization from a suitable solvent by conventional methods such as cooling, seeding, partial removal of the solvent from the solution, by adding an anti-solvent to the solution, evaporation, vacuum distillation, or a combination thereof.

The solvent used for isolating/recrystallizing the pure rivaroxaban of formula I is selected from the group consisting of water, acetone, methanol, ethanol, n-propanol, isopropanol, ethyl acetate, dichloromethane, toluene, N,N-dimethyformamide, dimethylsulfoxide, acetonitrile, acetic acid, and mixtures thereof. More specifically, the solvent is a mixture of water and dichloromethane.

In one embodiment, the isolation is carried out by adding water to the reaction mixture at a temperature of about 10° C. to about 35° C., and more specifically at a temperature of about 20° C. to about 30° C. After completion of addition process, the resulting mass is stirred at a temperature of about 10° C. to about 35° C. for at least 10 minutes, and most specifically at a temperature of about 20° C. to about 30° C. for about 15 minutes to about 2 hours.

The solid obtained is collected by filtration, filtration under vacuum, decantation, centrifugation, filtration employing a filtration media of a silica gel or celite, or a combination thereof.

The sulfonyl ester intermediate of formula III employed for the coupling reaction disclosed herein allows the product to be easily isolated and purified, thereby producing a product with 85-95% overall yield.

The highly pure rivaroxaban, or a stereochemically isomeric form or a racemic mixture thereof, obtained by the above process may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 90° C., and specifically at about 75°

C. to about 85° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer, and the like.

In another embodiment, the highly pure rivaroxaban obtained by the process disclosed herein has a total purity, includes both chemical and enantiomeric purity, of greater than about 99%, specifically greater than about 99.5%, more specifically greater than about 99.9%, and most specifically greater than about 99.95% as measured by HPLC. The HPLC purities were measured as per the method and conditions reported in column-2 of page No. 5905 of J. Med. Chem. 2005, 48, 5900-5908.

According to another aspect, there is provided a process for preparing rivaroxaban of formula I:

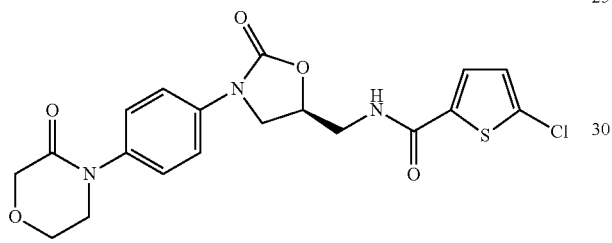

I or a stereochemically isomeric form or a racemic mixture thereof, comprising reacting a sulfonyl ester compound of formula III:

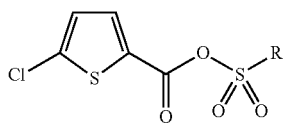

III wherein R is as defined above;
with 4-[4-[(5S)-5-(aminomethyl)-2-oxo-1,3-oxazolidin-3-yl]phenyl]morpholine-3-one of formula II:

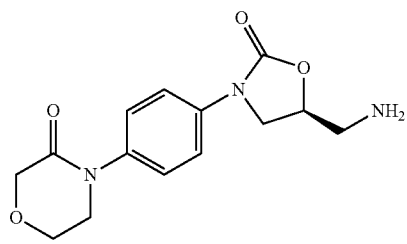

II or a stereochemically isomeric form or a racemic mixture thereof, or an acid addition salt thereof, to produce the rivaroxaban of formula I or a stereochemically isomeric form or a racemic mixture thereof.

According to another aspect, there is provided a process for preparing a sulfonyl ester compound of formula III:

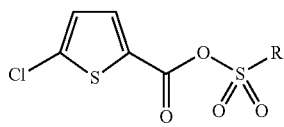

III wherein R is as defined above; comprising reacting 5-chlorothiophene-2-carboxylic acid of formula IV:

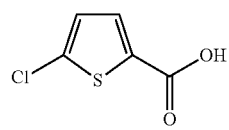

IV or a salt thereof, with a sulfonylating agent of formula Va or Vb:

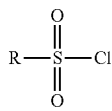

Va

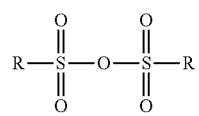

Vb wherein 'R' is an alkyl, cycloalkyl, haloalkyl, aralkyl, or substituted or unsubstituted aryl group; to produce the sulfonyl ester compound of formula III.

According to another aspect, there is provided a novel sulfonyl ester compound of formula III:

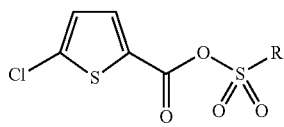

III wherein 'R' is an alkyl, cycloalkyl, haloalkyl, aralkyl, or substituted or unsubstituted aryl group.

Specifically, the group 'R' in the compounds of formula III is selected from the group consisting of methyl, ethyl, propyl, isopropyl, isobutyl, chloromethyl, fluoromethyl, trifluoromethyl, phenyl, p-tolyl, benzyl, 4-nitrophenyl, 4-chlorophenyl, 3-nitrophenyl, 4-chlorobenzyl, and the like; and most specifically, R is methyl or p-tolyl.

The following examples are given for the purpose of illustrating the present invention and should not be considered as limitation on the scope or spirit of the invention.

EXAMPLES

Example 1

Preparation of Rivaroxaban

1-Methylimidazole (24.6 g, 0.3 mol) was added to a stirred suspension of 5-chlorothiophene-2-carboxylic acid (16.25 g, 0.1 mol) in dichloromethane (162 ml) at 0-5° C. and the resulting solution was stirred for 10 minutes. A solution of methanesulfonyl chloride (12 g, 0.105 mol) in dichloromethane (40 ml) was added to the above solution at −5° C. The resulting solution was stirred for 1 hour at −5° C. to produce a reaction mass containing the sulfonyl ester intermediate, followed by portion wise addition of 4-[4-[(5S)-5-(aminomethyl)-2-oxo-1,3-oxazolidin-3-yl]phenyl]morpholine-3-one (29.1 g, 0.1 mol, chiral purity: 99.9%). The reaction mixture was stirred for 2 hours at 25-30° C., followed by the addition of water (162 ml) and then stirring for 15 minutes. The separated solid was filtered, washed with dichloromethane (50 ml) and water (100 ml), and the resulting wet material was dried at 80-85° C. for 3 to 5 hours to produce 39.2 g of pure rivaroxaban as a white crystalline solid (Theoretical Yield: 90%; Purity by HPLC: 99.9%; and Chiral Purity by HPLC: 99.9%).

Example 2

Preparation of Rivaroxaban 4-(N,N-dimethylamino)pyridine (36.6 g, 0.3 mol) was added to a stirred suspension of 5-chlorothiophene-2-carboxylic acid (16.25 g, 0.1 mol) in dichloromethane (162 ml) at 0-5° C. and the resulting solution was stirred for 10 minutes. A mixture of p-toluenesulfonyl chloride (19.05 g, 0.1 mol) and dichloromethane (50 ml) was added to the above solution at −5° C. The resulting solution was stirred for 1 hour at −5° C. to produce a reaction mass containing the sulfonyl ester intermediate, followed by portion wise addition of 4-[4-[(5S)-5-(aminomethyl)-2-oxo-1,3-oxazolidin-3-yl]phenyl]morpholine-3-one (29.1 g, 0.1 mol, chiral purity: 99.9%). The reaction mixture was stirred for 2 hours at 25-30° C., followed by the addition of water (162 ml) and then stirring for 15 minutes. The separated solid was filtered, washed with dichloromethane (50 ml) and water (100 ml), and the resulting wet material was dried at 80-85° C. for 3 to 5 hours to produce 37.3 g of pure rivaroxaban as a white crystalline solid (Theoretical Yield: 85.6%; Purity by HPLC: 99.9%; and Chiral Purity by HPLC: 99.9%).

Example 3

Preparation of Rivaroxaban

1-Methylimidazole (20.5 g, 0.25 mol) was added to a stirred suspension of 5-chlorothiophene-2-carboxylic acid (16.25 g, 0.1 mol) in dichloromethane (162 ml) at 0-5° C. and the resulting solution was stirred for 10 minutes. A solution of methanesulfonic anhydride (17.4 g, 0.1 mol) in dichloromethane (40 ml) was added to the above solution at −5° C. The resulting solution was stirred for 1 hour at −5° C. to produce a reaction mass containing the sulfonyl ester intermediate, followed by portion wise addition of 4-[4-[(5S)-5-(aminomethyl)-2-oxo-1,3-oxazolidin-3-yl]phenyl], morpholine-3-one (29.1 g, 0.1 mol, chiral purity by HPLC: 99.85%). The reaction mixture was stirred for 2 hours at 25-30° C., followed by the addition of water (162 ml) and then stirring for 15 minutes. The separated solid was filtered, washed with dichloromethane (50 ml) and water (100 ml), and the resulting wet material was dried at 80-85° C. for 3 to 5 hours to produce 38.5 g of pure rivaroxaban as a white crystalline solid (Theoretical Yield: 88.4%; Purity by HPLC: 99.8%; and Chiral Purity by HPLC: 99.85%).

Example 4

Preparation of 5-Chloro-N-[[2-oxo-3-[4-(3-oxomorpholin-4-yl)phenyl]oxazolidin-5-yl]methyl] thiophene-2-carboxamide (Racemic rivaroxaban)

1-Methylimidazole (24.6 g, 0.3 mol) was added to a stirred suspension of 5-chlorothiophene-2-carboxylic acid (16.25 g, 0.1 mol) in dichloromethane (162 ml) at 0-5° C. and the resulting solution was stirred for 10 minutes. A solution of methanesulfonyl chloride (12 g, 0.105 mol) in dichloromethane (40 ml) was added to the above solution at −5° C. The resulting solution was stirred for 1 hour at −5° C. to produce a reaction mass containing the sulfonyl ester intermediate, followed by portion wise addition of racemic 4-[4-[5-(aminomethyl)-2-oxo-1,3-oxazolidin-3-yl]phenyl]morpholine-3-one (29.1 g, 0.1 mol). The reaction mixture was stirred for 2 hours at 25-30° C., followed by the addition of water (162 ml) and then stirring for 15 minutes. The separated solid was filtered, washed with dichloromethane (50 ml) and water (100 ml), and the resulting wet material was dried at 80-85° C. for 3 to 4 hours to produce 39.1 g of pure racemic 5-chloro-N-[[2-oxo-3-[4-(3-oxomorpholin-4-yl)phenyl]oxazolidin-5-yl]methyl]thiophene-2-carboxamide as a white crystalline solid (Theoretical Yield: 90%; Purity by HPLC: 99.9%).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. A one-pot process for preparing rivaroxaban, 5-chloro-N-[[(5S)-2-oxo-3-[4-(3-oxomorpholin-4-yl)phenyl]oxazolidin-5-yl]methyl]thiophene-2-carboxamide, of formula I:

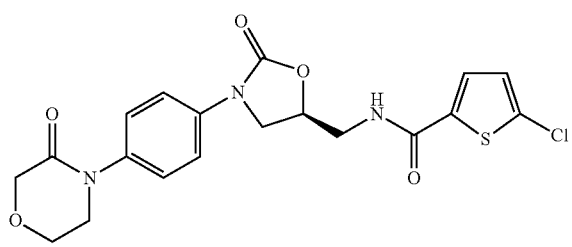

or a stereochemically isomeric form or a racemic mixture thereof, comprising:

a) reacting 5-chlorothiophene-2-carboxylic acid of formula IV:

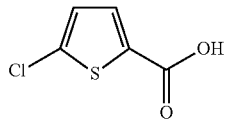

or a salt thereof, with a sulfonylating agent of formula Va or Vb:

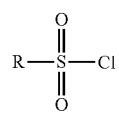

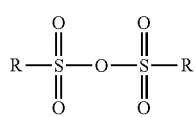

wherein 'R' is an alkyl, cycloalkyl, haloalkyl, aralkyl, or substituted or unsubstituted aryl group;
to produce a sulfonyl ester compound of formula III:

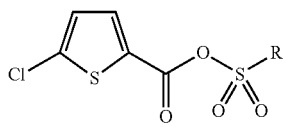

wherein R is as defined above;
b) reacting the sulfonyl ester compound of formula III with 4-[4-[(5S)-5-(aminomethyl)-2-oxo-1,3-oxazolidin-3-yl]phenyl]morpholine-3-one of formula II:

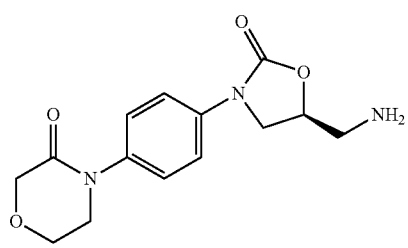

or a stereochemically isomeric form or a racemic mixture thereof, or an acid addition salt thereof, to produce the rivaroxaban of formula I or a stereochemically isomeric form or a racemic mixture thereof.

2. The process of claim 1, wherein the group 'R' in the compounds of formulae III, Va and Vb is selected from the group consisting of methyl, ethyl, propyl, isopropyl, isobutyl, chloromethyl, fluoromethyl, trifluoromethyl, phenyl, p-tolyl, benzyl, 4-nitrophenyl, 4-chlorophenyl, 3-nitrophenyl and 4-chlorobenzyl.

3. The process of claim 2, wherein the group 'R' in the compounds of formulae III, Va and Vb is methyl or p-tolyl.

4. The process of claim 1, wherein the one-pot process is carried out in the presence of a solvent or a mixture of solvents.

5. The process of claim 4, wherein the solvent is selected from the group consisting of a chlorinated hydrocarbon, an ester, a cyclic ether, an aliphatic ether, a hydrocarbon, a polar aprotic solvent, a nitrile, an alcohol, and mixtures thereof.

6. The process of claim 5, wherein the solvent is selected from the group consisting of dichloromethane, dichloroethane, chloroform, carbon tetrachloride, ethyl acetate, methyl acetate, isopropyl acetate, tert-butyl methyl acetate, ethyl formate, tetrahydrofuran, 2-methyl tetrahydrofuran, dioxane, diethyl ether, diisopropyl ether, methyl tert-butyl ether, monoglyme, diglyme, n-pentane, n-hexane, n-heptane, cyclohexane, toluene, xylene, acetonitrile, propionitrile, 4-methylmorpholine, N,N-dimethylformamide, N,N-dimethylacetamide, dimethylsulfoxide, methanol, ethanol, isopropanol, n-butanol, and mixtures thereof.

7. The process of claim 6, wherein the solvent is dichloromethane.

8. The process of claim 1, wherein the one-pot process is carried out in the presence of a base, wherein the base is an organic or inorganic base; and wherein the salt of the compound of formula IV is derived from an organic or inorganic base.

9. The process of claim 8, wherein the base is an organic base; and wherein the salt of the compound of formula IV is derived from an organic base.

10. The process of claim 8, wherein the organic base is selected from the group consisting of trimethylamine, tributylamine, triethylamine, diisopropylethylamine, N-methylmorpholine, 4-(N,N-dimethylamino)pyridine and 1-alkylimidazole; and wherein the inorganic base is selected from the group consisting of sodium hydroxide, calcium hydroxide, magnesium hydroxide, potassium hydroxide, lithium hydroxide, sodium carbonate, potassium carbonate, sodium bicarbonate, potassium bicarbonate, lithium carbonate, sodium tert-butoxide, sodium isopropoxide and potassium tert-butoxide.

11. The process of claim 10, wherein the organic base is 1-alkylimidazole or 4-(N,N-dimethylamino)pyridine.

12. The process of claim 11, wherein the organic base is 1-methylimidazole.

13. The process of claim 1, wherein the overall one-pot process is carried out at a temperature of about −15° C. to about the boiling temperature of the solvent used.

14. The process of claim 13, wherein the overall one-pot process is carried out at a temperature of about −5° C. to about 30° C.

15. A process for preparing rivaroxaban of formula I:

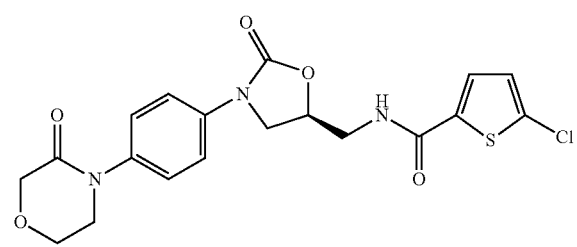

or a stereochemically isomeric form or a racemic mixture thereof, comprising reacting a sulfonyl ester compound of formula III:

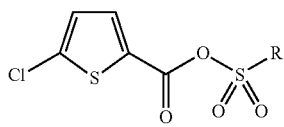

wherein 'R' is an alkyl, cycloalkyl, haloalkyl, aralkyl, or substituted or unsubstituted aryl group;

with 4-[4-[(5S)-5-(aminomethyl)-2-oxo-1,3-oxazolidin-3-yl]phenyl]morpholine-3-one of formula II:

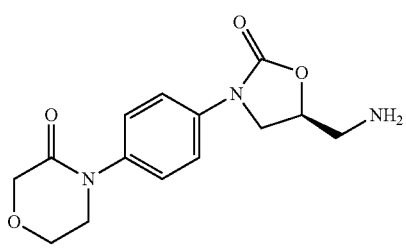

or a stereochemically isomeric form or a racemic mixture thereof, or an acid addition salt thereof, to produce the rivaroxaban of formula I or a stereochemically isomeric form or a racemic mixture thereof.

16. A process for preparing a sulfonyl ester compound of formula III:

wherein 'R' is an

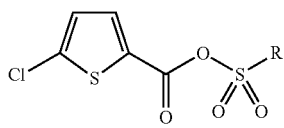

alkyl, cycloalkyl, haloalkyl, aralkyl, or substituted or unsubstituted aryl group; comprising reacting 5-chlorothiophene-2-carboxylic acid of formula IV:

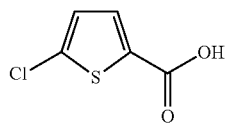

or a salt thereof, with a sulfonylating agent of formula Va or Vb:

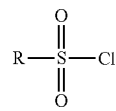

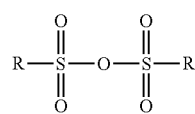

wherein 'R' is an alkyl, cycloalkyl, haloalkyl, aralkyl, or substituted or unsubstituted aryl group; to produce the sulfonyl ester compound of formula III.

17. A sulfonyl ester compound of formula III:

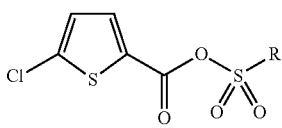

wherein 'R' is an alkyl, cycloalkyl, haloalkyl, aralkyl, or substituted or unsubstituted aryl group, with the proviso that the said group 'R' does not include methyl, trifluoromethyl and p-tolyl.

18. The compound of claim 17, wherein the group 'R' is selected from the group consisting of ethyl, propyl, isopropyl, isobutyl, chloromethyl, fluoromethyl, phenyl, benzyl, 4-nitrophenyl, 4-chlorophenyl, 3-nitrophenyl and 4-chlorobenzyl.

* * * * *